United States Patent [19]
Rogers

[11] Patent Number: 6,002,967
[45] Date of Patent: Dec. 14, 1999

[54] DIATHERMY APPARATUS WITH AUTOMATIC TUNING FOR APPLICATOR HEAD

[75] Inventor: Noel A. Rogers, Overland Park, Kans.

[73] Assignee: International Medical Electronics, Ltd., Kansas, Mo.

[21] Appl. No.: 08/824,563

[22] Filed: Mar. 26, 1997

[51] Int. Cl.[6] .................................................. A61B 05/00
[52] U.S. Cl. .......................................... 607/101; 607/156
[58] Field of Search .................................. 607/101–100, 607/154–156

[56] References Cited

U.S. PATENT DOCUMENTS

| | | | |
|---|---|---|---|
| 3,800,802 | 4/1974 | Berry et al. | 128/404 |
| 4,068,292 | 1/1978 | Berry et al. | 361/437 |
| 4,210,152 | 7/1980 | Berry | 128/422 |
| 4,281,362 | 7/1981 | Berry | 361/437 |
| 4,510,937 | 4/1985 | Rogers | 128/422 |
| 5,683,382 | 11/1997 | Lenihan et al. | 607/156 |
| 5,693,082 | 12/1997 | Warner et al. | 607/156 |
| 5,776,176 | 7/1998 | Rudie | 607/154 |

*Primary Examiner*—Robert L. Nasser
*Attorney, Agent, or Firm*—Shook, Hardy & Bacon, L.L.P.

[57] ABSTRACT

A diathermy apparatus has a power circuit operative at a selected, fixed frequency. An applicator head, for providing therapeutic treatment, has an irradiating portion. A transmission line connects the power circuit and applicator head, and is of a length so that, at the frequency, a selected minimum power is delivered to the applicator head when unloaded, the length further being such that a selected maximum amount of power is delivered to the applicator head when it is in a loaded position in close proximity to a patient load. The diathermy apparatus also includes a cabinet and portable base, wherein the portable base mounts the applicator head, and provides a carriage for the cabinet. The applicator head has an internal fan for cooling components of the applicator head. A display is provided for displaying the actual power consumed by the patient load. A processor independently controls the pulse modulator and power circuit in digital increments on a selected scale.

6 Claims, 3 Drawing Sheets

DIATHERMY APPARATUS WITH AUTOMATIC TUNING FOR APPLICATOR HEAD

BACKGROUND OF THE INVENTION

1. Field of the Invention

The present invention relates in general to a diathermy apparatus which therapeutically heats internal body tissue by irradiating the tissue with RF energy. In particular, the present invention discloses a method and apparatus for accurately measuring and controlling the amount of RF power being absorbed by the body tissue with the irradiating region of the diathermy apparatus. Specifically, the present invention relates to a diathermy apparatus which automatically tunes an applicator head of the apparatus.

2. Description of the Related Art

Medical diathermy involves the use of high frequency electric current for the therapeutic treatment of body tissue. This technique involves the transcutaneous transmission of high frequency energy to internal body tissues. The irradiated RF energy generates heat within the internal body tissue, having a therapeutic effect. This deep heating action produced by the diathermy apparatus is used to treat a number of varied ailments.

A diathermy apparatus typically generates high frequency electric currents which are provided to an applicator head for controllable application to the body tissue to be treated. The high frequency currents produced in a diathermy apparatus typically have a standard frequency of 27.12 MHz, which is within the permissible frequency range allocated for diathermy service. At this frequency, nerves and muscles are not adversely stimulated by the radiated energy, and the temperature produced in the internal body tissue is well below that required to destroy the tissue or impair its vitality.

Prior art diathermy machines typically are constructed of a single cabinet which houses the electrical circuitry and the display portion of the shortwave electrical therapeutic apparatus. Typically, a pair of movable arms extend outwardly from the cabinet, each of which positions a diathermy head at its outer end.

The applicator head of the diathermy apparatus includes a radiating electrode which is comprised of an induction coil that generates electromagnetic and electrostatic energy in response to the high frequency electric currents flowing through the electrode. The generated electromagnetic and electrostatic energy is then controllably applied by the applicator head to the body of the patient. This energy causes heat to be generated in the internal body tissue, which is within the radiating region of the head. U.S. Pat. No. 3,800,802 entitled "Short-Wave Therapy Apparatus" to Berry, et al., issued Apr. 2, 1974, and U.S. Pat. No. 4,210,152 to Berry entitled "Method and Apparatus for Measuring and Controlling the Output Power of a Shortwave Therapy Apparatus", issued Jul. 1, 1980, disclose diathermy machines which are utilized to apply RF energy to the human body for therapeutic purposes. These patents are incorporated herein by reference.

Of the energy generated by a diathermy apparatus, only the electromagnetic energy is useful in therapy. The electrostatic energy field that is generated simply heats the surface area of the human skin without deep penetration, and is therefore undesirable. Electrostatic shields, of the type shown, in U.S. Pat. No. 4,068,292 to Berry, et al. entitled "Electrostatic Shield for Diathermy Treatment Head", issued Jan. 10, 1978, and U.S. Pat. No. 4,281,362 to Berry entitled "Electrostatic Shield for Diathermy Treatment Head", issued Jul. 28, 1981, are conventionally used to attenuate the electrostatic energy field. These patents are incorporated herein by reference. U.S. Pat. No. 4,510,937 to Rogers entitled "Method and Apparatus for Operating Dual Diathermy Applicator Heads in Close Proximity to One Another", issued Apr. 16, 1985, discloses a method and apparatus for simultaneously operating two diathermy treatment heads in close proximity without interference caused by phase and frequency differences. This patent is incorporated herein by reference.

Elimination of the electrostatic field, through the use of an electrostatic shield, significantly improves the operating efficiency of the diathermy apparatus and the accuracy of the power measurement. Particularly, the interposition of an electrostatic shield between the generating electrode and the applicator head and the treated body tissue significantly reduces the electrostatic (capacitive) coupling between the body tissue and the applicator head, thereby making the reactive parameters of the head less responsive to the surface characteristics of the human load within the irradiating region of the applicator head. By eliminating capacitive coupling between the applicator head and the body tissue, the operating parameters of the diathermy apparatus no longer vary erratically in response to the surface characteristics of the load within the irradiating region of the head. Since the operating parameters of the device do not vary in response to the surface characteristics of the load, the level of power being provided to the applicator head only varies in response to the level of power actually being absorbed by the treated body tissue. While the introduction of body tissue into the irradiating region of the applicator head still causes some minor disturbances in the electrical operation of the power generating equipment, these disturbances are much smaller in magnitude and can be accurately measured. Furthermore, these minor disturbances are predictable and can be accounted for during the power computation.

Elimination of the electrostatic field also stabilizes the operation of the diathermy apparatus because the applicator head is less likely to be detuned from resonance on the introduction of a load into the irradiating region of the head. Therefore, it is easier to keep the current voltage locked in phase, thereby greatly enhancing the operation of the diathermy apparatus and improving the accuracy of the power measurement.

In order to properly and efficiently utilize the electromagnetic field that is generated by the applicator head of the diathermy apparatus, the circuitry associated with the apparatus should be tuned and the power applied to the patient should be closely controlled at a desired level. As the patient moves, or the body temperature or circulation of the patient changes, the load can vary rather widely. To compensate for such expected changes in the load, tuning devices are desirable because they continuously maintain the head tuned to a resonate condition to assure maximum power transfer from the applicator head to the patient load.

In the past, a variety of mechanical tuning components have been utilized for tuning the applicator head to a resonate condition. For example, variable capacitors have been utilized so that an operator of the diathermy apparatus could manually adjust the capacitor to maintain the device in a tuned state. Many such devices utilized a servo mechanism to achieve the tuning. Typically, the prior art utilizes a variable capacitor and a mechanical motor for physically driving the capacitor. The motor is coupled to a servo mechanism which controls a tuning element in the applicator head. The tuning element (e.g., variable capacitor) is varied in order to keep the applicator head in electrical resonance, thereby maintaining phase lock between the sensed current and voltage, and thus maintaining the amount of power being absorbed by the treated body tissue at a desired level.

The mechanical tuning mechanisms utilized in the prior art which require the operator to continuously vary the power are undesirable because of the very requirement that the operator must continually monitor and adjust the device. Those prior art devices requiring variable capacitors, servo mechanism and motors are overly cumbersome, require multiple components, and increase the overall expense of the device, and are therefore undesirable.

The need exists for a diathermy apparatus for generating and providing RF power in a simple manner. The need also exists for a diathermy apparatus which is more portable than prior art machines, and which automatically tunes the diathermy apparatus in a simple and efficient manner. The need also exists for a diathermy apparatus which easily and accurately displays on visual presentation of the actual power being used by a satellite load. These and other needs are met by the unique diathermy apparatus of the present invention while the foregoing and other drawbacks of the prior art are overcome.

SUMMARY OF THE INVENTION

It is an object of the present invention to provide an efficient diathermy apparatus.

It is an object of the present invention to automatically tune an applicator head of a diathermy apparatus.

It is an additional object of the present invention to provide a diathermy apparatus which is portable.

It is a further object of the present invention to provide a diathermy apparatus which is easy to operate.

It is another object of the present invention to visually display a representation of power generated by a diathermy apparatus and consumed by a patient load.

It is an additional object of the present invention to provide a diathermy apparatus having a cabinet which is removable from a portable housing, so that the diathermy apparatus can be utilized in the field.

These and other objects are achieved by a unique diathermy apparatus for applying RF energy to a load of human tissue for therapeutic purposes. The apparatus of the present invention has a cabinet for housing the control circuitry of the apparatus. A control panel is provided at one face of the housing for presenting display areas and input keys and switches. Each of a pair of handles is also provided on the control panel face for gripping by an operator or user when moving the housing. Each of a pair of transmission lines extends from the control circuitry within the housing to a respective applicator head located remotely from the housing.

The diathermy apparatus of the present invention also provides a portable base constructed in the form of a generally rectangular box having an open top. Wheels, for portability, are provided at a lower portion of the portable base. A pair of movable arms extend outwardly from one side of the portable base. Each of the diathermy applicator heads is mounted on an outer end of a respective one of the arms. The open top of the portable base is dimensioned so as to snugly receive the diathermy cabinet. When inserted into the portable base, the control panel is accessible at the open top of the portable base. The handles on the face of the control panel may be grasped by an operator for insertion and removal of the cabinet. Such a construction permits the cabinet to be placed within the portable base, and the entire unit moved into a desired location.

Alternatively, the cabinet can be removed from the base and put on a rack or shelf, possibly along with other medical electronic devices, leaving the portable base free to be moved into the desired location. Additionally, in accordance with an aspect of the invention, the cabinet has connectors for receiving the diathermy arms. Accordingly, the cabinet can be removed from the portable base, the movable arms and diathermy heads can be removed from the portable base, and the cabinet, arms, and head can be placed in a carrying case. An operator can thus carry the unit into the field, and reconnect the diathermy arms directly to the cabinet.

Each diathermy applicator head of the present invention has at least one capacitive element, and at least one inductive control element positioned within a case. An electrostatic shield serves as a cover for the case. In accordance with an aspect of the present invention, a small fan, including fan blades and a motor, is positioned within the applicator head case for cooling of the head and its components.

Inside the housing, a processor and a crystal oscillator, operative at 27.12 MHz, are connected to a pulse width modulator. The output of the pulse width modulator is connected in series through preliminary power amplifier circuits, having an output connected to a final power amplifier circuit. The final power amplifier includes a low pass filter, for filtering harmonics, and a bridge circuit for detecting standing wave ratios. The standing wave ratio bridge circuit has an output, connected by a transmission line, to an applicator head of the invention. The standing wave ratio circuit, which acts as a detector, is also connected in a feedback loop through an amplifier circuit and into a light bar display.

The pulse width modulator is utilized to modulate the RF frequency provided by the crystal oscillator. Modulation of the frequency provides the rate at which power is to be applied during therapy to a patient load.

In accordance with the principles of the present invention, the rate at which power may be supplied is variable in frequency from a first, minimum selected frequency, of 300 pulses per second, to a second, maximum selected frequency of 7,000 pulses per second. The processor is programmed to permit the rate to be varied by an operator on a digital scale from a minimum unit of one to a maximum unit of 12. Thus, a setting of one unit represents 300 Hz and a setting of 12 units represents 7,000 Hz.

The processor also controls the power to be applied to the applicator head. The present invention is preferably constructed to permit variance in power output from a desired minimum power to a desired maximum power, preferably approximately 100 watts. The desired processor is programmed to permit an operator to vary the power on a digital scale from one unit to 12 units, where one unit represents minimum power and 12 units represents approximately 100 watts. The processor also includes a timer to permit an operator to program the time duration of therapy. Preferably, the processor is constructed to permit time duration to be set in 5 minute increments, with 5 minutes being a minimum, and 60 minutes being a maximum. A display is connected to the processor for displaying digital read outs of the rate, power and time settings. A keyboard input, coupled to the processor, is utilized by an operator to change the display up or down, depending upon the desired rate, power, and time desired for a given diathermy treatment.

The amount of power generated by the diathermy system is determined by the setting provided by the operator through the input means, and by the processor accordingly controlling the pulse width of each pulse. The RF energy leaving the pulse width modulator is amplified by the preliminary power amplifiers and applied to a final amplifier that amplifies the power to the desired power setting.

The low pass filter, for filtering subharmonics, leads into a variable standing wave ratio (VSWR) bridge circuit that is used as a detector to detect the forward wave of power being delivered to the applicator head. The VSWR bridge output is also utilized to drive a light bar display showing representative power actually being delivered to the head, and thus ultimately to the patient. The light bar display is constructed of a plurality of light emitting diodes (LEDs), each of which represent a defined and selected incremental amount of power to the patient. In accordance with an aspect of the invention, the apparatus is calibrated so that each light bar represents an actual amount of power. Thus, the apparatus provides a unique visual display permitting an operator to visually ascertain whether the appropriate amount of power is being delivered to the patient.

The diathermy apparatus of the present invention is also uniquely designed to maintain resonance, and therefore optimal coupling of the diathermy energy to the patient load, when the diathermy head is in a loaded, close-proximity position to the patient load. Similarly, the construction is such that removal of the applicator head from the load causes the apparatus to deliver a minimum or zero power to the applicator head.

Particularly, each applicator head of the diathermy apparatus of the present invention includes an inductive element formed in a coil, and a capacitive element made up of a number of capacitive components. For example, the capacitive element of the applicator head is made up of physical aluminum plates located between the spiral wound inductor and the inside back portion of the aluminum case, a fixed, stray capacitance made up of the many different capacitor plates to case ground, and the stray capacitance between the inductor and the electrostatic shield utilized in the applicator head. As will be understood, a variable capacitance is also realized when the irradiating portion of the head is located in close proximity to a load of human tissue, thus absorbing the inductive heating present from the tuned circuit of the applicator head.

In accordance with an aspect of the present invention, yet another capacitive element is obtained by designing the length of the transmission line cable, extending from the power amplifier final stage and coupling into the resonate circuit of the applicator head in a fashion that at a frequency of 27.12 MHz, the following parameters are realized.

When the applicator head is resting in an open case position—that is, no power is being delivered to the load—then, transmission line connecting the power amplifier final stage and the resonate circuit of the applicator head reflects an open voltage or high impedance to the amplifier, resulting in a selected minimum power (or no power) being utilized by the diathermy apparatus. Thus, the apparent net capacitance at the end of the transmission line is a minimum value which allows the resonate point of the final power amplifier to increase to a frequency of approximately 27.16 to 27.18 MHz, thereby unloading the final power amplifier and the power supplies that feed DC voltage and current into the final power amplifier.

When, however, the applicator head is placed in close proximity to a patient load, the variable capacitance element starts to increase, thus increasing the capacitance at the end of the transmission line. Variable standing wave ratios, indicative of the capacitance increase, reflect back into the final power amplifier, causing the amplifier to adjust to increase the current supplied to the applicator head, thus increasing the power to the selected level. Thus, when the applicator head is unloaded, the load presented to the final RF power amplifier is a high impedance. Under such a condition, the final power amplifier requires only minimal power from the switching power supply. Additionally, under such a condition, the preliminary power amplifier becomes unloaded.

BRIEF DESCRIPTION OF THE DRAWINGS

The objects and features of the invention noted above are explained in more detail with reference to the drawings, in which like reference numerals denote like elements, and in which.

DETAILED DESCRIPTION OF THE INVENTION

Figures 1, 2:
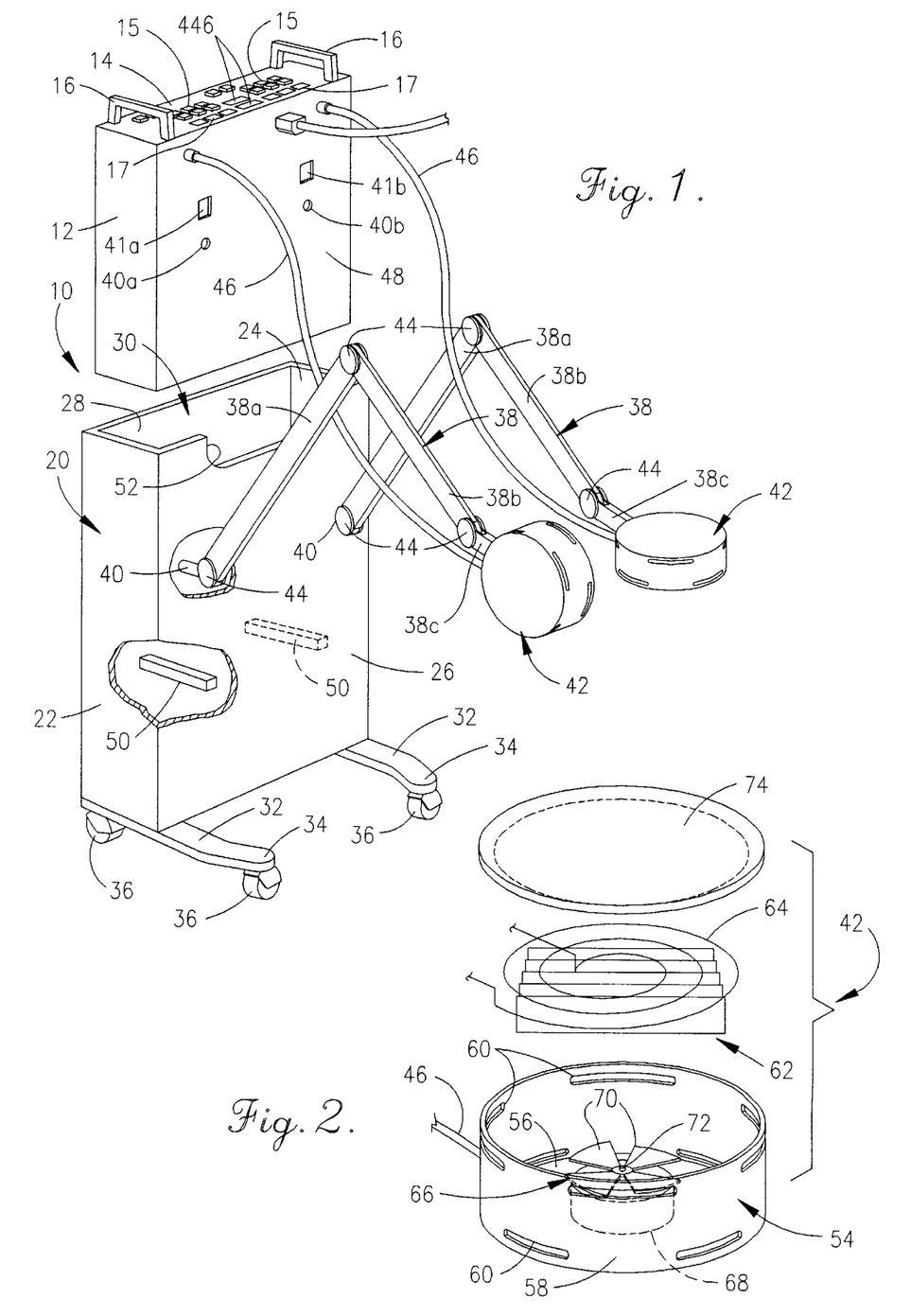
FIG. 1 is a perspective view of the physical form of the diathermy apparatus of the present invention.
FIG. 2 is an exploded perspective view illustrative of an applicator head of the diathermy apparatus of the present invention.

With reference initially to FIG. 1, a diathermy apparatus of the present invention is denoted generally by reference numeral 10. Diathermy apparatus 10 has a cabinet 12, for housing electronic components of the apparatus 10. As illustrated, housing 12 is preferably generally rectangular in configuration, having four sides, a bottom and a top. In the preferred embodiment, the top face 14 of cabinet 12 includes a control panel for controlling the electronic circuitry of the diathermy apparatus 10. The central panel includes input keys 15 and display areas 17. Top face 12 has a pair of handles 16, each of which is located proximate an outer side edge of the cabinet 12.

Diathermy apparatus 10 of the present invention also includes a portable base, designated generally by reference numeral 20. Portable base 20 serves as a carriage for cabinet 12. As illustrated, portable base 20 of diathermy apparatus 10 is preferably constructed in a generally rectangular box configuration, with an open top. Specifically, portable base 20 has first and second outer side walls, or faces 22, 24, and front and rear faces or walls, 26, 28, respectively. Portable base 20 has an open top, designated by reference numeral 30. In the preferred embodiment shown, portable base 20 includes a pair of support brackets 32 positioned at the bottom of portable base 20. Each support bracket 32, preferably positioned on the bottom of portable base 20, extends outwardly past the front face 26 of the portable base 20. An outermost end 34 of each supporting bracket 32 angles inwardly, toward the other support member 32, as illustrated. Castor wheels 36 are positioned on the bottom side surface of each support 32 at outer ends thereof, as illustrated.

Front wall 26 of portable base 20 mounts a pair of outwardly extending, movable arms 38. Each movable arm 38 is mounted to front wall 26 of portable base 20 by a mounting support 40. Each movable arm 38 is extendable and supports an induction applicator head 42 thereon.

Particularly, in the preferred embodiment, each extendable arm 38 is formed of three sections, designated by 38a, 38b, and 38c, rotationally attached to each other at pivot points 44. Each arm 38 is attached to its respective mounting support 40 by a similar rotational attachment 44. Each movable arm 38 is hingedly attached to its respective mounting support 40, such that the arm 38 can be swung sideways relative to the front wall 26 of support base 20. Similarly, as will be readily appreciated, each movable arm may be pivoted upwardly and downwardly relative to front wall 26 of portable base 20. Additionally, as illustrated in FIG. 1, each applicator head 42 is pivotally attached to its respective movable arm 38, such that the heads 42 can be moved between horizontal and vertical positions. The entire unit is constructed so that the movable arms 38 will remain in a substantially preset positioned, but may be pivotally moved, and thus swung, extended, or contracted, with a controllable amount of force. The construction illustrated gives the applicator treatment heads 42 a great deal of movement for optimum positioning with respect to the patient or patient's body (or patients' bodies).

With reference still to FIG. 1, each diathermy applicator head 42 is connected by a coaxial transmission line 46 to the electrical circuitry of the diathermy apparatus located inside the housing formed by cabinet 12. In this regard, each coaxial cable 46 extends through a front wall 48 of cabinet 12 to connect with the electrical circuitry of diathermy apparatus 10, as described in greater detail below with reference to the schematic electrical diagrams. Each coaxial transmission line 46 also connects with the circuit inside the respective diathermy applicator head 42, as described in greater detail below.

In accordance with an aspect of the present invention, cabinet 12, housing the electrical components of the diathermy apparatus 10, is insertable into, and removable from, portable base 20. Particularly, an operator may grasp each handle 16 on the top face of cabinet 12, and lower cabinet 12 through the opening 30 of portable base 20 into the interior of portable base 20 defined by walls 12, 22, 24, 26, and 28 of the portable base 20. As illustrated, a pair of support brackets 50 are fixedly located in the interior space of portable base 20, and connect to inside surfaces of front and rear walls 26, 28, respectively. When inserted into portable base 20, the bottom of cabinet 12 rests on the top of support brackets 50. Preferably, when cabinet 12 is fully inserted into portable base 20, the top face 14 of cabinet 12, having the control panel, is either flush with the top of portable base 20, or extends slightly above the top of portable base 20. As shown, front wall 26 of portable base 20 has a cut-out area 52, at a central, upper portion thereof, so that coaxial transmission lines 46, as well as a power supply line 54, entering into front wall 48 of cabinet 12, may extend from cabinet 12 and pass portable base 20 in an uninterrupted fashion.

The physical construction of diathermy apparatus 10 permits it to be easily moved into an optimum position with respect to a patient load for operation of the apparatus 10. Additionally, cabinet 12 may be removed from portable base 20 and placed on a fixed shelf unit or rack, while portable base 20 may still be positioned as desired. Portable base 20, without cabinet 12 located in its interior, is much lighter and more easily moved. Moreover, the construction of the present invention permits the cabinet 12 to be located, for instance, on a rack and the portable base 20 moved from room to room or location to location, as needed. Alternatively, portable base 20 could remain in a particular hospital room, for instance, and the removable cabinet 12 could be relocated and utilized in conjunction with a second portable base 20 at another location. Additionally, the unique construction of the diathermy apparatus 10 makes the electrical components far more accessible for serviceability than in prior art constructions.

With reference now to FIG. 2, a diathermy applicator head 42 of the present invention is shown and described in detail.

Applicator head 42 of the present invention has a casing 54, preferably formed of aluminum and covered by plastic. Casing 54 has a rear face 56 and a peripheral side wall 58. Peripheral side wall 58 has a plurality of spaced apart slots 60 positioned as shown. A plurality of capacitor plates 62, having a known capacitance, are positioned inside casing 54. An inductive coil element 64, having a known inductance, is also positioned within casing 54.

A small fan, denoted generally by reference numeral 66 includes a motor, located inside a motor housing 68, and an impeller formed of a number of fan blades 70, rotatably mounted to an output shaft of the motor at a hub 72. The fan 66 is positioned centrally within the casing 54 on the inside surface of rear face 56 of casing 54. Fan 66 is powered by a power supply, and is operated to cool the components of applicator head 42.

An electrostatic shield 74 serves as a front cover for applicator head 42. As described above, the electrostatic shield 74 eliminates, or at least drastically reduces, the electrostatic energy emitted from applicator head 42, thereby significantly improving the operating efficiency of the diathermy apparatus 10. Coaxial transmission line 46 connects electrical circuitry within cabinet 12 with the circuit formed of capacitor plate 62 and inductive coil element 64.

Figure 3:
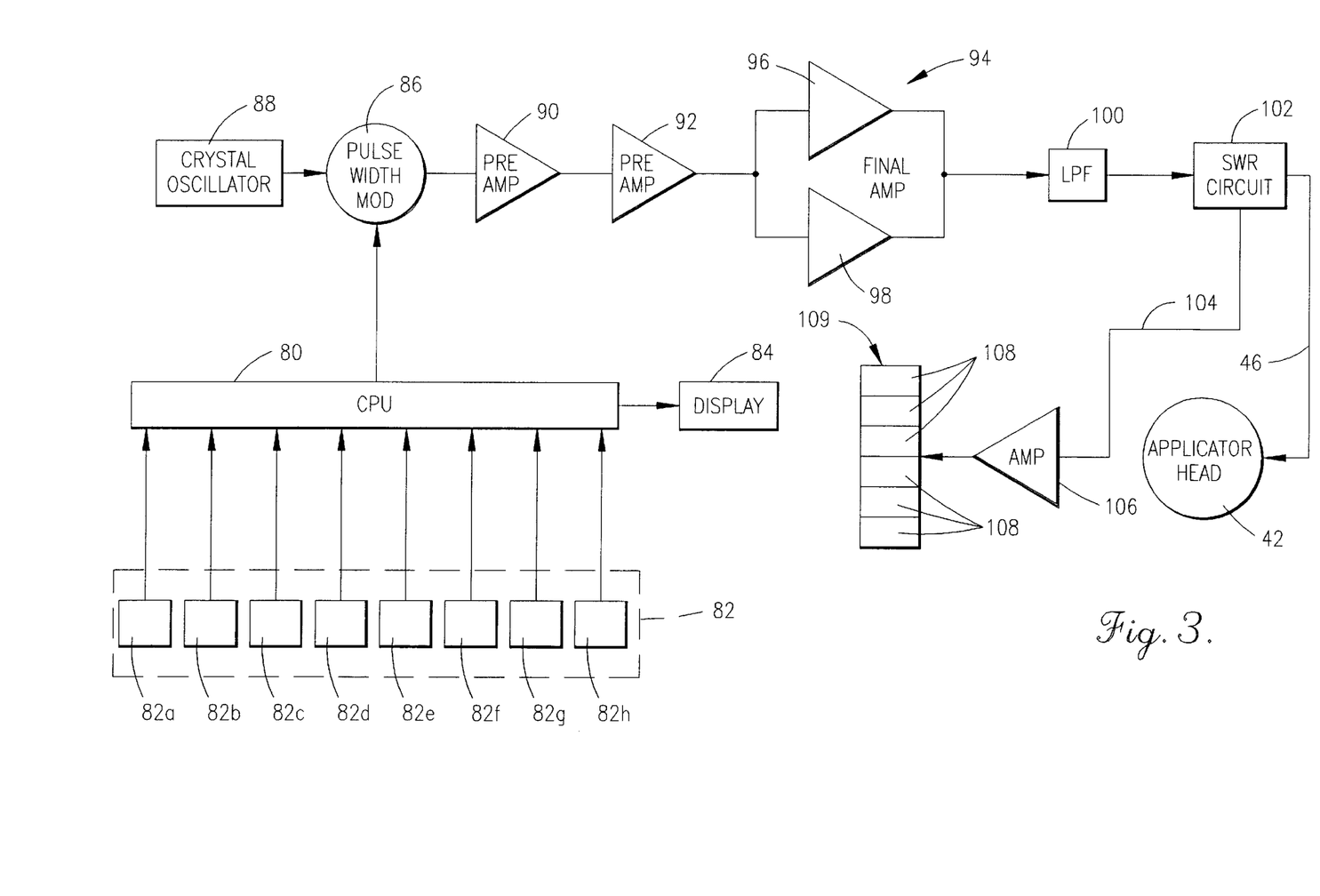
FIG. 3 is a block diagram of the electrical circuitry of the diathermy apparatus of the present invention.

With reference now to FIG. 3, a block diagram illustrating the electrical circuitry associated with diathermy apparatus 10 of the present invention is shown and described.

Diathermy apparatus 10 includes a central processing unit (CPU), designated generally by reference numeral 80 and referred to herein as a processor. A plurality of code switches, for coding processor 80 are designated generally by reference numeral 82, and are utilized for encoding processor 80. A display 84 is connected to processor 80. Display 84, as described in greater detail below, preferably includes a plurality of display modules for displaying rate, power, and time settings selected by an operator of diathermy apparatus 10. Processor 80 is connected to a pulse width modulator 86. An RF crystal oscillator, designated by reference numeral 88, operates at a frequency of 27.12 MHz and is used to provide an accurate means for supplying the RF frequency of the diathermy apparatus 10. As will be readily understood, the high frequency electrical currents induced in diathermy apparatus 10 will thereby have a standard frequency of approximately 27.12 MHz, which is within the permissible frequency range allocated for diathermy service.

Pulse width modulator 86 outputs into a preliminary power amplifier formed of a pair of preliminary power amplifiers 90, 92 connected in series. Preliminary power amplifier 92 outputs into a final power amplifier circuit, designated generally by reference numeral 94, and formed generally of final power amplifiers 96, 98 connected in parallel, as illustrated. Final power amplifier 94 includes a low pass filter 100 for filtering off subharmonics in a known manner. Low pass filter 100 outputs into an SWR circuit designated by reference numeral 102. SWR circuit 102 outputs into an applicator head 42. As described in greater detail below, SWR circuit 102 reflects standing wave ratios back into final power amplifier 94. SWR circuit 102 also reflects forward waves of power through line 104, through an amplifier 106, and into a litebar display 108. Litebar display 108 is preferably formed of a plurality of light emitting diodes 109 (LEDs), wherein each diode 109 represents an actual amount of power delivered to the applicator head 42, and hence a patient load.

It should be understood that diathermy apparatus 10, as illustrated in FIG. 1, preferably includes a pair of applicator heads 42. Each applicator head 42 is independently controlled, having its own associated circuitry as illustrated in FIG. 3.

Applicator head 42 is illustrated as having a fixed capacitance C2 (approximately 36 pF and a fixed inductance L2 (approximately 950 nH). Fixed capacitance C2 represents the capacitance of the capacitor plate 62, as illustrated in FIG. 2, while fixed inductance L2 represents the inductance of inductor coil element 64, as set forth in FIG. 2. Also, fan 66 (see FIG. 2) is connected as shown. It will be understood by those with skill in the art that applicator head 42, in addition to the physical aluminum capacitance plates 62 and the physical inductive element, comprised of coil 64, includes an additional fixed capacitance. The additional capacitance is made up of the many different capacitor plates, to case ground, as well as the stray capacitance between the inductor element 64 and the electrostatic shield 74. As will be described in greater detail below, a variable capacitance is realized when the radiating portion of applicator head 42 is located close to human tissue, thus absorbing the inductive heating resulting from the tuned circuit condition of the present invention. Additionally, in accordance with an aspect of the invention, another important capacitive element is obtained by designing the length of the coaxial cable comprising transmission line 46, in a fashion that at the fixed frequency of 27.12 MHz certain parameters, as described above and as set forth in greater detail below, are realized.

In operation, upon activation of diathermy apparatus 10, electrical power is provided to the apparatus, and the processor 80 is initialized. In accordance with the desired diathermy therapeutic treatment, the operator utilizes keys 15 on the control panel of the diathermy apparatus to enter a desired power setting, rate of application, and time duration. Particularly, each key 15 on the control panel corresponds with one of the code switches 82. In the preferred embodiment, switch 82a corresponds to "power up". Switch 82b corresponds to "power down". Switch 82c corresponds to "rate up". Switch 82d corresponds to "rate down". Switches 82e and 82f correspond to "stop" and "start", respectively. Switches 82g and 82h correspond to "time up" and "time down", respectively. Accordingly, upon initialization of diathermy apparatus 10, the operator utilizes switch 82a and/or 82b to enter a preferred power. As discussed above, processor 80 is programmed to accept input from switches 82a and 82b to correlate operation of the switches with a programmed digital scale. Preferably, processor 80 is programmed with a digital "power scale" from 1–12, with one representing a desired small amount of power, while a unit of 12 represents a maximum amount of power, which is preferably approximately 100 watts. Accordingly, switches 82a and 82b are utilized by the operator to incrementally or decrementally alter the desired power set. Switches 82c, 82d are similarly used to vary the rate, or frequency of application of the power. In the preferred embodiment, the processor is programmed to accept rate variations on a digital scale from 1–12. Preferably, a unit of one represents 300 Hz, while a unit of 12 represents 7,000 Hz. As will be understood by those skilled in the art of diathermy apparatus, molecules in a patient's blood are excited at a different rate, depending upon the rate setting for application of power. This can become important, depending upon the particular patient receiving therapy. For example, a high power setting corresponds with deep penetration into the patient load, and therefor deep therapeutic benefit. However, in a patient having poor circulation, a high power setting along with a high rate setting could very likely begin to burn the surface of the patient's skin. Therefore, it is common practice to reduce the rate of power application to prevent burning, while keeping power at a high setting for good therapeutic benefit. Switches 82g and 82h are utilized to select the time duration of therapy, while switches 82e and 82f are utilized to start and stop, respectively, application of therapy with diathermy apparatus 10.

By way of an example in accordance with the preferred operating principles of the diathermy apparatus 10 of the present invention, when diathermy apparatus 10 is turned on, the digital read outs on the display areas 17, read 12-12-5, representing rate of 12, power of 12, and time of 5 minutes. As discussed, keyboard type entry is utilized by the operator to change the digital display up or down, depending upon the desired rate, power, and time for a given diathermy treatment. In the example given, with a digital display reading of 12-12-5, upon pressing the start key 82f, diathermy apparatus 10 will deliver a rate of 7,000 pulses per second, and approximately 100 watts of power for a time of 5 minutes. Thus, data indicative of a desired power of 100 watts, at the rate of 7,000 pulses per second, is generated by processor 80 and applied to pulse width modulator 86 (FIG. 3) so as to modulate (e.g., turn on and off) RF crystal oscillator 88, thereby generating the desired approximately 100 watts of power. The RF energy leaving the pulse width modulator 86, enters the preliminary power amplifier 90. In accordance with the preferred principles of the present invention, preliminary power amplifier 90,92 amplify the signal to a 15 watt level. The RF energy is then applied to final power amplifier 94, where it is amplified to the desired 100 watt level. Thus, crystal oscillator 88 stabilizes the frequency at 27.12 MHz. The preamplifier amplifies the signal the first time, while the final power amp amplifies the signal to the desired level. Pulse width modulator 86 generates a square pulse, based upon data indicative of the desired rate and power provided by processor 80, depending upon what was keyed into the keyboard. As the energy passes through the final power amplifier 94, it passes through a low pass filter which filters off the second, third, fourth, and fifth harmonics of the fundamental. The energy then passes through SWR bridge 102, and passes along transmission line 46 to applicator head 42.

In accordance with an aspect of the present invention, the total line length of the transmission line 46, extending between the final amplifier to the tune circuit of applicator head 42, is critical to give the needed variable capacitance at the end of the transmission line 46. Thus, the hardware components of the circuitry, including those components having an inductance and a capacitance at the applicator head, as well as the transmission line, are utilized to effect change in the capacitance from, in the preferred embodiment, approximately one-half (½) picofarad(Pf) to approximately 3½ Pf. This change in capacitance represents the desired amount of capacitance change on the applicator head 42 to change its tuning from roughly 250 ohms of effective impedance, down to approximately 50 ohms of effective impedance. When 50 ohms of effective impedance is reached, the amplifier 94 draws approximately 12 amps of current and output approximately 100 watts of power when the head is in a loaded position in close proximity to a patient load, and a maximum power setting is selected at the controller. In contrast, if the head is unloaded, and thus removed from its position in close proximity to the patient load, the capacitance's value at the end of the transmission line is down to approximately ½ Pf, and the final power amplifier 94 sits at an idle current of approximately 3 amps in the preferred embodiment, and is delivering very little power out to the applicator head 42, and thus the patient load. In the preferred embodiment, a minimal amount of power output to the applicator head represents loss in the circuit elements.

As will now be understood, changing the effective capacitance at the end of the transmission line 46, and thus at the applicator head 42, from approximately ½ Pf to 3½ Pf represents tuning of a tuned circuit, which represents going from a low load condition wherein the applicator head 42 is removed from a patient load to a loaded condition, wherein the applicator head 42 is located in close proximity to a patient load.

As diathermy apparatus 10 is operated, an applicator head 42 is placed in close proximity to a patient load, thereby changing the effective capacitance at the applicator head to the desired maximum amount, the selected amount of power is output through applicator head 42 into the patient load. The unique design of the present invention is such that the line length is selected to produce the desired results at the selected fixed frequency, in this case 27.12 MHz. As power is transmitted to the patient load, SWR bridge circuit 102 reflects standing wave ratios back to the final power amplifier 94. Final power amplifier 94 responds to the received standing wave ratio, and current is increased or decreased accordingly to maintain power at the desired level. As conditions at the patient load changes, such as may be caused by movement of the patient closer to or farther away from the applicator head 42, or as may be caused by a rise in temperature of the patient load, the condition of the electrical circuit also changes, as will be readily understood. In practice, as the inductance at the load increases, final power amplifier 94, based upon reflected standing wave ratios, will adjust to output less electrical current, and hence less electrical power. In contrast, as the capacitance at the load increases, the final power amplifier 94 will adjust to increase electrical current, and thus increase the electrical power transmitted through applicator head 42 to the patient load. In other words, the final power amplifier 94 receives reflected standing wave ratios and works as a tank circuit to maintain resonance while the applicator head 42 is in close proximity to the patient load.

By way of a specific example, when applicator head 32 is placed in close proximity to a human load, variable capacitance starts to increase at the end of transmission line 46. In the preferred embodiment, transmission line 46 is a 50 ohm line and thus, the line is considered matched (or flat) when the load is 50 ohms and the driving source is 50 ohms. In other words, the variable standing wave ratio is 1 to 1. In contrast, the transmission line 46 is mismatched when the variable standing wave ratio is increased to 15 to 1. A $\lambda_m$ of line length is given by the following formula:

$$\lambda_m = \frac{300}{f}(e_r)$$

Where $\lambda_m$ equals wave length in meters, f equals frequency in MHz and $e_r$ equals coefficient of dielectric constant for the cable 46 in the design (preferably 67%).

The science of transmission line theory teaches if a ¼ wave line is open at one end, a short or very low impedance will be present at the other end. In other words, a high voltage, low current at one end, produces a low voltage, high current at the other end. This principal is used in the design and construction of the present invention, including the several elements of applicator head 42. For example, the exact diameter of the coil to obtain the desired inductance for inductive element 64, the exact coupling capacity from the end of the line 46 to the fixed capacitance plates to obtain a portion of the desired capacitance are determined. Importantly, the exact length of the line 46 is selected to match the elements in the applicator head to the final power amplifier so as to obtain a high impedance, typically 250 ohms or more when the head is in an unloaded position, and a low impedance, preferably 50 ohms when the applicator head is positioned in close proximity to a human load. In the loaded position, the final power amplifier will deliver power, at the selected rate, for the selected time, to the human load. A 50 ohm load is reflected from the applicator head 42 to the final power amplifier, via the coaxial transmission line 46. The ratio of approximately 15 to 1 in power consumption can be realized by apparatus 10 utilizing the foregoing principles. For example, a switching power supply capable of delivering 150 watts (12 volts at 13 amps) will deliver the 150 watts when the load (applicator head in close proximity to the body) is matched (e.g., 50 ohms to 50 ohms). Conversely, the apparatus will deliver only approximately 5 watts when the applicator head is unloaded (e.g., 250 ohms at the end of the line).

Additionally, during operation of diathermy apparatus 42, standing wave ratio bridge circuit 102 reflects forward power via line 104 to litebar display 108. Particularly, SWR circuit 102 detects RF energy at the applicator head. Thus, the time constant selected by components of SWR circuit 102 are selected so that the detector sees only the peak energy, so that the detection will also fall off before the next energy pulse comes along. The detected peak energy is scaled through an operational amplifier 106 and sent to litebar display 108, for illuminating an appropriate number of LEDs 109, representative of the actual power being delivered to applicator head 42. This unique display technique provides the operator or technician with a constant visual representation of the actual power delivered to the patient load. In accordance with the preferred aspects of the present invention, each LED 109 represents a selected, actual amount of power, such as 10 watts. Thus, ten LEDs 109, all illuminated, would indicate that a full 100 watts of power was being delivered to the patient load, whereas, for instance, only 3 LEDS illuminated would indicate that only approximately 30 watts were being delivered to the patient load.

Figure 4:
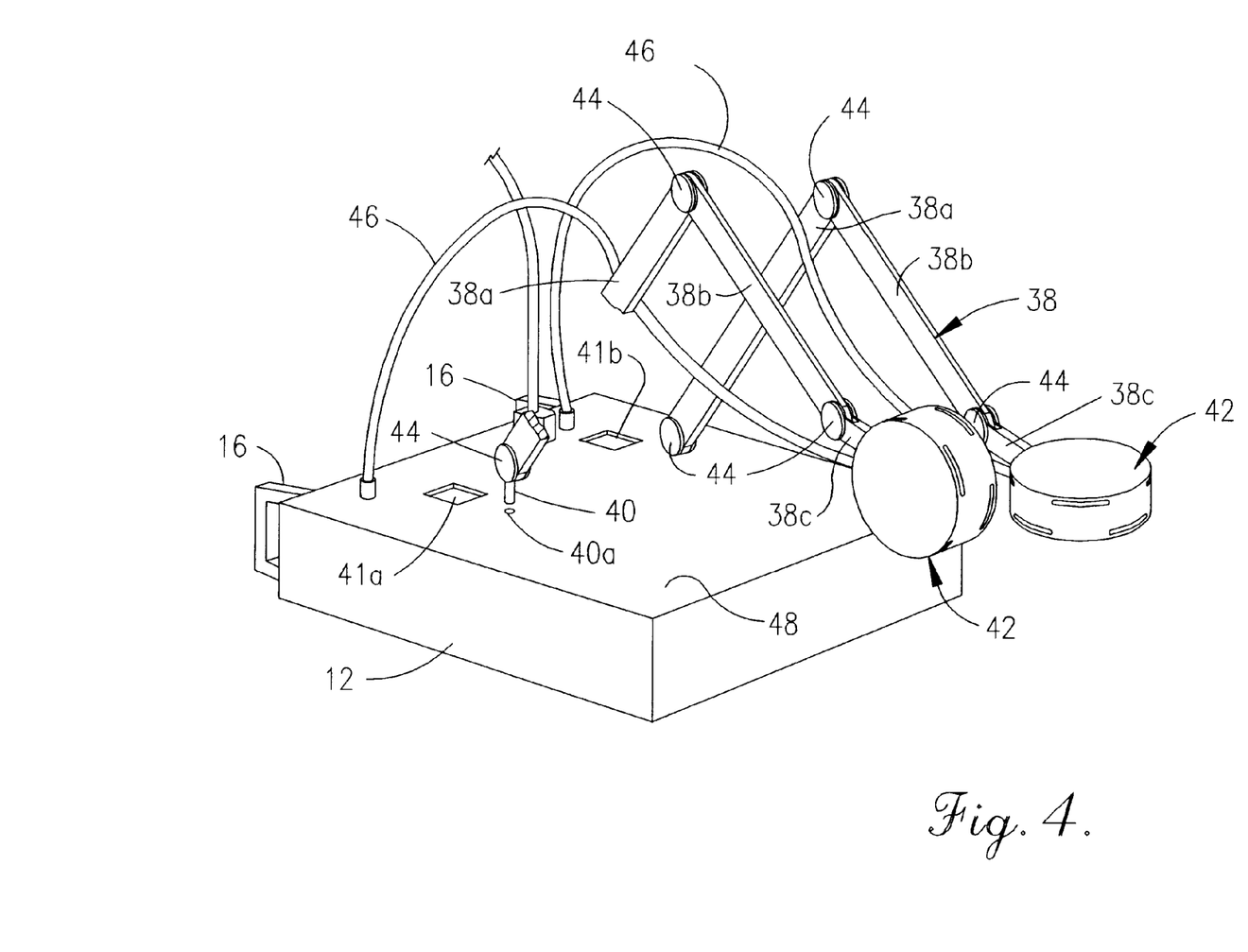
FIG. 4 is a perspective view showing the movable arms of the diathermy apparatus attached directly to the cabinet so that the cabinet can be placed on a flat surface and used without the possible base.

In some situations, it may be desirable to place the diathermy apparatus on a flat surface such as a table. The construction of the present invention provides this option. As shown in FIG. 4, the arms 38 can be detached from the base and attached to the front wall 48 of the cabinet 12. This is accomplished by removing the mounting supports 40 for the arms from the base 20 and securing them in openings 40a and 40b (FIG. 1) formed in wall 48. The cabinet 12 can then be used with its back resting on a table surface (or other flat) and its front wall 48 facing upwardly in the position shown in FIG. 4.

As illustrated and described, diathermy apparatus 10 is uniquely constructed so that cabinet 12 is removable from portable base 20. In use, cabinet 12 may be removed from portable base 20 and placed in a carrying case (not shown).

Additionally, movable arms 38 and diathermy heads 42 may be removed from their mounting position on portable base 20, and located in the carrying case. In such a manner, the cabinet 12, arms 38, and heads 42 may be carried out of the field for use. Thus, the construction of the present invention permits the diathermy unit to be conveniently transported to a patient, rather than requiring the patient to come to the diathermy apparatus. In use in the field, diathermy apparatus 10 is placed on a flat surface in the position as shown in FIG. 4, and mounting posts 40 of respective movable arms 38 are pivotally positioned within respective openings 40a, 40b, and movable arms 38 are pivoted as needed to located diathermy heads 42 in the desired location relative to a patient. FIG. 4 also illustrates elapsed timer indicators 41a, 41b, which record the total time diathermy 10 has been on.

From the foregoing it will be seen that this invention is one well adapted to attain all ends and objects hereinabove set forth together with the other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative, and not in a limiting sense.

What is claimed is:

1. A diathermy apparatus comprising:

a power circuit operative at a selected fixed frequency;

an applicator head having an irradiating portion, at least one inductive element, and at least one capacitive element;

a transmission line, connecting said power circuit and said applicator head, said transmission line of a length selected so that, at said selected fixed frequency, a selected minimum power is delivered to said applicator head when said applicator head is positioned at least a first distance from a load, said transmission line length further being such that a selected maximum power is delivered to said applicator head when said applicator head is positioned at a selected location in close proximity to said load.

2. The diathermy apparatus as set forth in claim 1, said power circuit further comprising:

a power amplifier powered by a constant voltage;

a detector circuit for detecting standing waves in said applicator head, wherein said standing waves vary with a change in said load, and reflect into said power circuit, and wherein said power amplifier responds to said standing waves by adjusting to maintain power delivered to said applicator head at a desired level when said applicator head is in close proximity to said load.

3. The diathermy apparatus as set forth in claim 2, said power circuit further comprising:

a responsive circuit for operating in a resonate condition when said applicator head is in close proximity to said load; and a low pass filter connected between said detector circuit and said responsive circuit.

4. The diathermy apparatus as set forth in claim 3, wherein the greater the inductance at the load, the less the power output by said power circuit, and wherein the greater the capacitance of said load, the greater the power output by said power circuit.

5. The diathermy apparatus as set forth in claim 2, further comprising:

a display connected to said detector.

6. The diathermy apparatus as set forth in claim 5, wherein said display comprises a light bar display for providing a visual indication of a level of power delivered to said load.

\* \* \* \* \*